United States Patent [19]

Slocum et al.

[11] Patent Number: 4,571,589

[45] Date of Patent: Feb. 18, 1986

[54] BIOMEDICAL IMPLANT WITH HIGH SPEED, LOW POWER TWO-WAY TELEMETRY

[75] Inventors: Chester D. Slocum; John R. Batty, Jr., both of Miami, Fla.

[73] Assignee: Cordis Corporation, Miami, Fla.

[21] Appl. No.: 443,446

[22] Filed: Nov. 22, 1982

[51] Int. Cl.$^4$ .................. G08C 19/06; A61N 1/00
[52] U.S. Cl. .................. 340/870.32; 128/419 PG; 128/631; 340/870.19
[58] Field of Search ............ 128/419 PG, 419 PT, 128/631, 903; 340/870.19, 870.20, 870.23, 870.24, 870.32, 825.54, 825.14, 825.20; 604/65–67; 343/6.8 LC; 370/100, 103, 104

[56] References Cited

U.S. PATENT DOCUMENTS

| | | | |
|---|---|---|---|
| 2,850,726 | 9/1958 | Steele | 340/870.23 |
| 3,727,616 | 4/1973 | Lenzkes | 128/422 |
| 3,942,535 | 3/1976 | Schulman | 128/419 PS |
| 4,196,418 | 4/1980 | Kip | 340/825.31 |
| 4,203,063 | 5/1980 | Loeb | 340/870.23 |
| 4,223,679 | 9/1980 | Schulman | 128/419 PT |
| 4,232,679 | 11/1980 | Schulman | 128/419 PG |
| 4,237,900 | 12/1980 | Schulman | 128/903 |
| 4,305,397 | 12/1981 | Weisbrod | 128/419 PT |
| 4,361,153 | 11/1982 | Slocum et al. | 128/419 P |
| 4,399,437 | 8/1983 | Falck | 340/825.72 |
| 4,416,282 | 11/1983 | Saulson | 128/419 PG |
| 4,416,283 | 11/1983 | Slocum | 128/419 PG |
| 4,424,812 | 1/1984 | Lesnick | 128/419 PG |
| 4,435,698 | 3/1984 | Klett | 340/870.19 |

OTHER PUBLICATIONS

"A Digital Phase Modulator and Demodulator for a Biomedical Telemetry System", Medical and Biological Engr., Jan. 1974, Ivison and Robinson.

Ko, Hynecek, and Homa, Single Frequency RF Powered ECG Telemetry System, IEEE Transactions, vol. BME-26, No. 2, Feb. 1979.

Zelina, Vamuakas, Lin, Neuman, Telemetry Pulse-Frequency Demodulation System, IEEE Conferences Session 12, 1979.

*Primary Examiner*—John W. Caldwell, Sr.
*Assistant Examiner*—Michael F. Heim
*Attorney, Agent, or Firm*—Henry W. Collins; George H. Gerstman

[57] ABSTRACT

For inbound data transmission a carrier signal is gated by the external programmer to transmit bursts of discrete numbers of cycles. The carrier is picked up by an implanted telemetry coil. The bursts are amplified and decoded by "missing pulse" detection. Outbound telemetry is synchronized with the external constant carrier in a similar manner by loading the coil for discrete numbers of cycles. In the preferred embodiment, within an eight cycle bit period, two cycles of 64 kHz carrier represent "0" while a six cycle burst represents "1", to achieve a two-way data transmission rate of 8000 bits per second.

18 Claims, 6 Drawing Figures

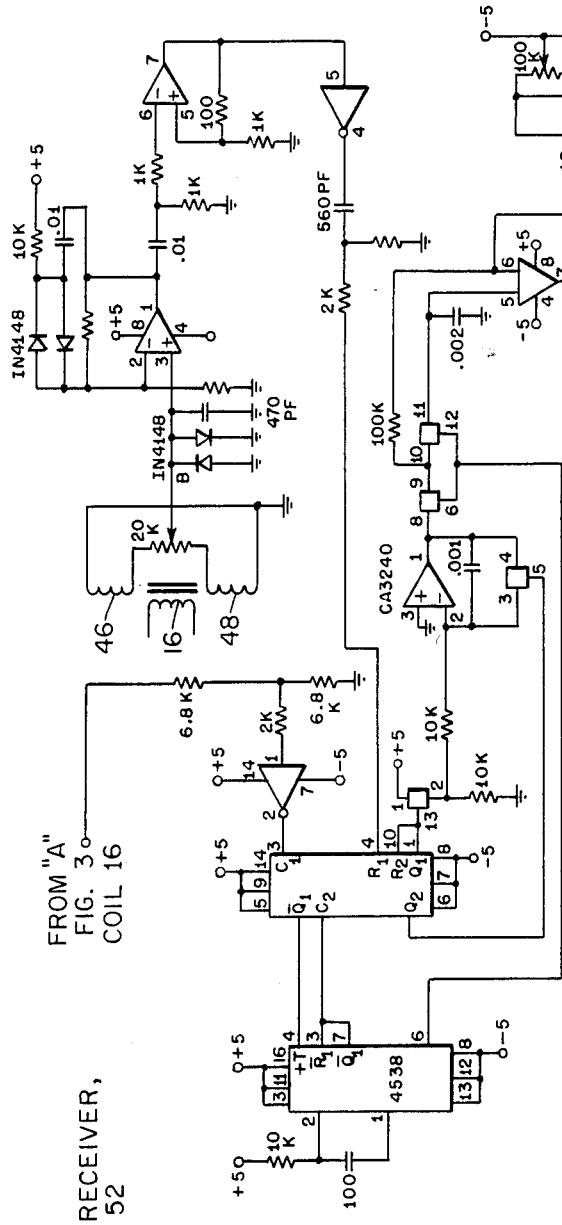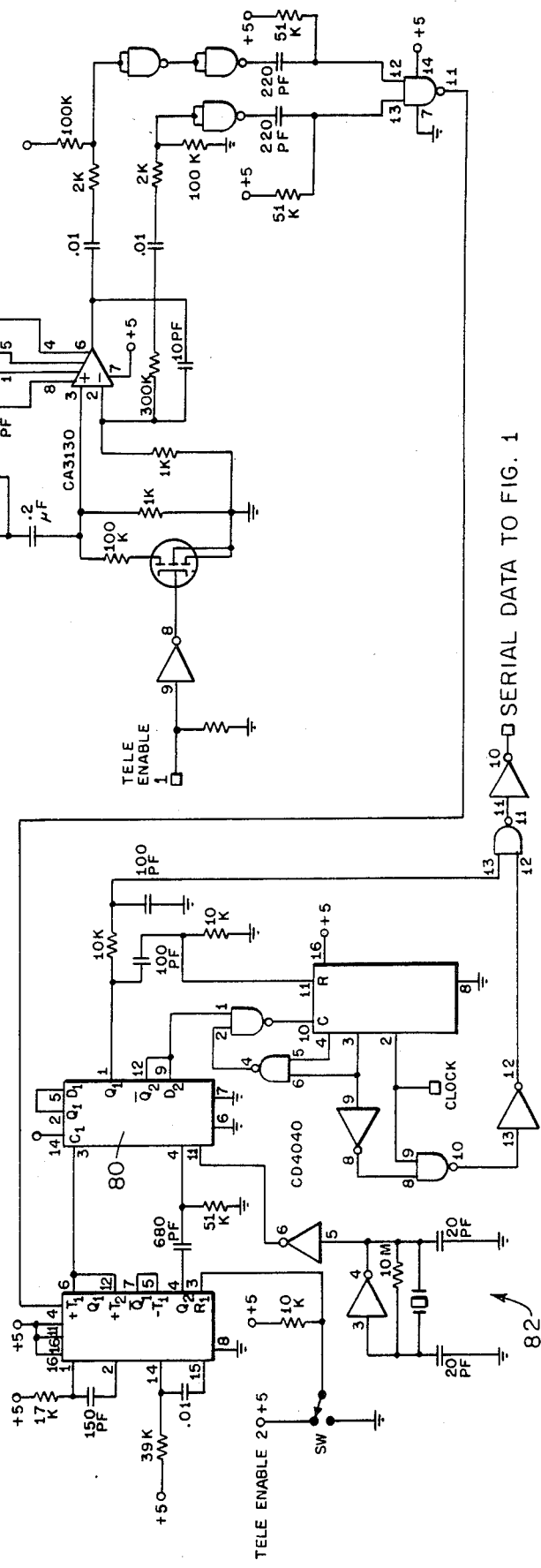
FIG. 4

BIOMEDICAL IMPLANT WITH HIGH SPEED, LOW POWER TWO-WAY TELEMETRY

CROSS-REFERENCE TO RELATED APPLICATIONS

This application is related to the following U.S. patent applications, assigned to the assignee of the present application, each of which is incorporated by reference in its entirety herein:

"Implant Telemetry System", Slocum et al, U.S. Ser. No. 153,093 filed May 27, 1980, now U.S. Pat. No. 4,361,153, issued Nov. 30, 1982; Divisional Application Ser. No. 406,367, filed Aug. 9, 1982, now U.S. Pat. No. 4,494,545, issued Jan. 22, 1985;

"Implantable Externally Programmable Microprocessor-Controlled Tissue Stimulator", Lesnick, U.S. Ser. No. 195,665 filed Oct. 9, 1980, now U.S. Pat. No. 4,424,812, issued Jan. 10, 1984;

"Interactive Programmer for Biomedical Implantable Devices", Mumford et al, U.S. Ser. No. 281,011 filed July 6, 1981, now U.S. Pat. No. 4,432,360, issued Feb. 21, 1984; and "Magnetic Reedless Switch for Biomedical Implantable Device", Slocum, U.S. Ser. No. 297,746 filed Aug. 31, 1981, now U.S. Pat. No. 4,416,283, issued Nov. 22, 1983.

BACKGROUND OF THE INVENTION

The invention relates generally to electromagnetic signalling and telemetry for biomedical implantable devices.

The increasing versatility of implanted stimulators such as cardiac pacers demands more complex programming capabilities. Programming in this context means noninvasively transferring parameter value data from an external device called the programmer to an internal device implanted in the patient's body. Outbound telemetry has been used in the past primarily to verify the programmed pulse parameters of implanted stimulators.

A number of programming systems have been successfully employed in commercially available cardiac pacers, including magnetic programming and radio frequency (RF) programming. Magnetic programming relies on the generation of a series of strong magnetic impulses which actuate a reed switch inside the pacer. The output of the reed switch circuit forms the programming input to data registers in the implant as shown, for example, in U.S. Pat. No. 3,805,796 to Terry et al, assigned to the assignee of the present application. In pacers such as the Cordis "Omnicor ®" series, the number of reed switch closures in sequence from 1 to approximately 135 is counted. The resulting count corresponds to a selected value of a specific parameter. Reed switches have a number of desirable attributes. Besides having little or no associated current drain in the quiescent mode, the insensitivity of reed switches protects against spurious programming. In addition, of course, it is possible to use the same sensor for the conventional diagnostic mode accessed by placing a permanent magnet over the pacer site. On the other hand, reed switch rates are limited to several hundred hertz, and, as pointed out in copending application Ser. No. 297,746, their physical size and sensitivity to orientation and proximity of the magnetic field are limitations. Moreover, electromagnetic programming requires a heavy coil and large current drain which increases the size and weight of the self-contained hand-held programming unit.

Reflected signal telemetry, introduced in copending application Ser. No. 153,093, has proved to be a significant advance in the art of implant telemetry. In this system, a 16 kHz carrier is externally transmitted and picked up and reflected by a coil in the implant capacitively tuned to the same frequency. A data-drive FET switch intermittently shunts the tuned coil thus modulating its reflectance characteristics. The data is recovered externally by pickup coils which feed the reflected signal through a relative phase shift detection system. The only power needed to operate the FET switch is supplied by the tuned coil transponder. 16 kHz was chosen because the customary titanium enclosure or "can" for present day pacers is relatively transparent to this frequency. In fact, the roll off above 20 kHz is at the rate of about 3 db per 30 kHz.

The amount of data flowing back and forth between the external programmer and the biomedical implant is on the increase. Programming requirements place ever greater strains on outbound as well as inbound telemetry. Outbound telemetry of intracardiac ECG's, for example, is a special challenge for low power implanted systems.

SUMMARY OF THE INVENTION

Accordingly, the general purpose of the present invention is to increase the data rate of two-way telemetry between the implant and the external programmer without an increase in size or power consumption.

For outbound telemetry, despite the far greater attenuation by the can, the frequency of the carrier signal is increased 64 kHz. For inbound data transmission, the same carrier is pulsewidth modulated in bursts of discrete numbers of whole cycles. The carrier is picked up by the same telemetry coil in the implant where the bursts are amplified and converted into wide and narrow pulses by a missing pulse detector. Outbound telemetry is also synchronized with the carrier by employing a portion of the inbound receiver circuitry to generate a synchronizing clock signal. In the preferred embodiment, the bit period is eight cycles long. Two cycles of 64 kHz carrier represent a binary "zero" while a six cycle burst represents a "1". This system achieves a data rate of 8,000 bits per second in either direction. This data rate has sufficient capacity for larger programming data flow and 125 microsecond bit period gives sufficient resolution for real time intracardiac ECG transmission.

BRIEF DESCRIPTION OF THE DRAWINGS

FIG. 4 is a schematic diagram of the external receiver of FIG. 1.

FIG. 1 illustrates the functional components of a two-way telemetry system for an implanted biomedical device. The system is designed specifically for implanted stimulators such as cardiac pacers. Cardiac pacers typically include an implantable "pulse generator" having electronic circuitry electrically connected to a pair of long flexible pacing leads which extend from the pulse generator pervenously, terminating in electrodes situated inside the heart. The typical implant enclosure comprises a relatively thin flat metal case as shown in copending application Ser. No. 153,093, U.S. Pat. No. 4,361,153 (FIG. 5), preferably a deep drawn container made of titanium, and a sealed epoxy neck portion through which the pacing leads are connected.

Figure 1:
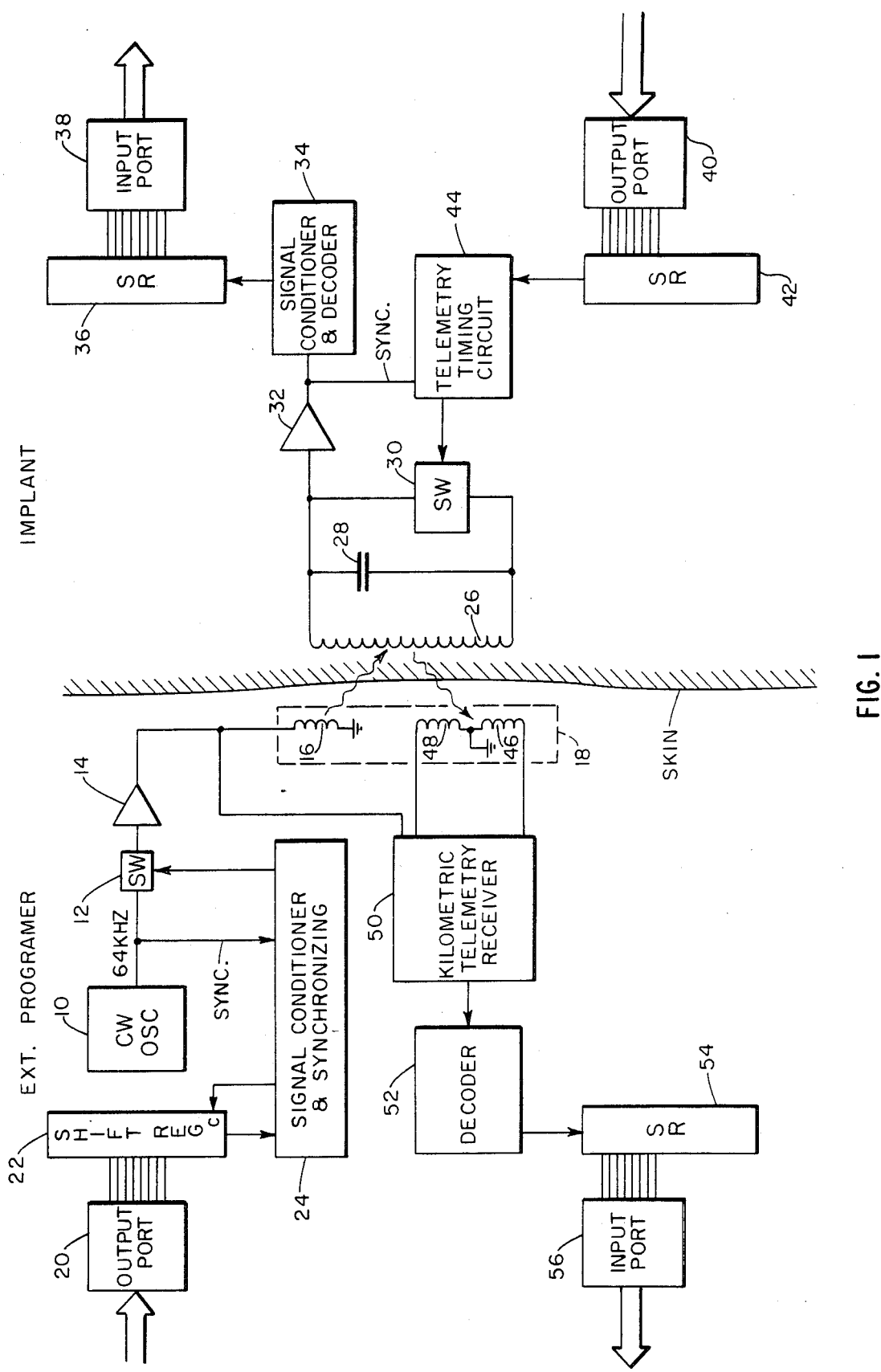
FIG. 1 is a block diagram of the two-way telemetry system according to the invention.

The implant circuitry shown in FIG. 1 of the present application is confined to two-way communications with the external programmer. The functions performed by the implant, such as cardiac stimulation, are assumed to be microprocessor-based, communications with the system as a whole being accomplished via a typical 8 bit input/output port associated with a microcomputer. Similarly, the external programmer system shown in FIG. 1 is confined to components needed for communication with the implant. The external programmer is assumed to include a microprocessor-based programming system of the type disclosed in copending application Ser. No. 281,011, U.S. Pat. No. 4,432,360, inbound and outbound data being presented via parallel 8 bit input/output ports associated with the particular microcomputer system used in the programmer.

In the external programmer communications system, a continous wave oscillator 10 generates a 64 kHz carrier signal which is passed via analog switch network 12 which may be envisioned as being normally closed during the receive mode and normally open during the transmit mode to a power amplifier 14. The output of the power amplifier drives series connected transmitter coil 16. Coil 16 forms a part of a triad coil assembly 18 located in the programmer head as shown in copending application Ser. No. 153,093, U.S. Pat. No. 4,361,153.

For inbound telemetry, data to be communicated from the programmer to the implant is presented in parallel bit form at a microcomputer output port 20. The bit lines of the output port 20 are connected to the parallel load terminals of a conventional shift register 22.

Figure 2:
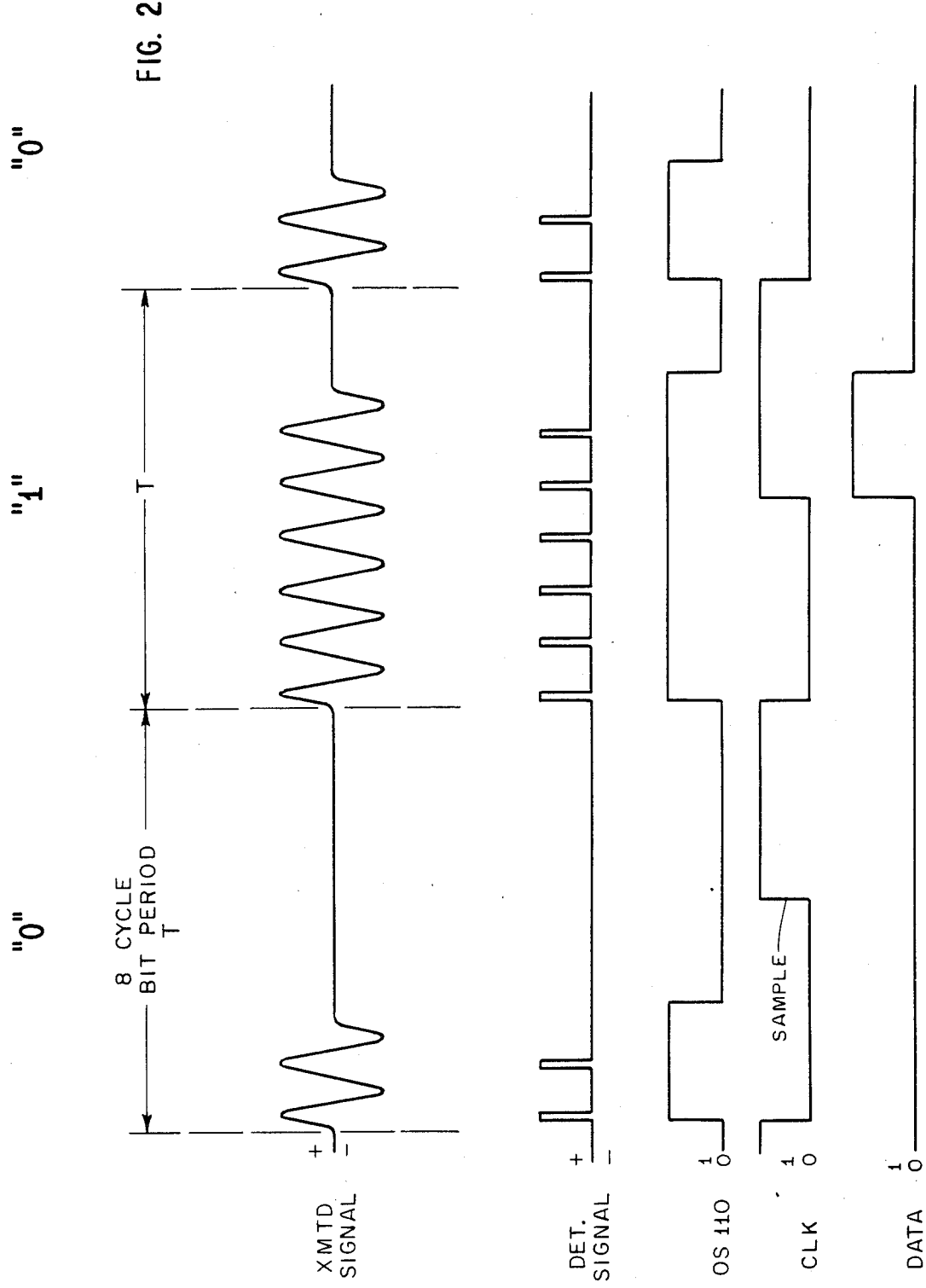
FIG. 2 is a composite waveform diagram illustrating the carrier modulation and demodulation according to the invention.

The signal conditioner and synchronizing circuit 24 gates the carrier signal to the amplifier 14 in the following manner. As the contents of shift register 22 are shifted out serially, each bit of a data word or byte (8 bits in a row) is presented one at a time. For each eight cycles of the carrier, one bit is clocked out of the shift register. If the bit is zero, the switch 12 is closed to gate exactly two cycles of the carrier signal through the power amplifier to the coil 16, as shown in FIG. 2. For a binary "1", exactly six cycles of the carrier are gated continuously to the transmitter coil.

Inside the implant, because of the proximity of the programmer's transmitter coil 16, the field generated thereby is picked up on the implant telemetry coil 26 which is tuned by means of parallel capacitor 28. In the inbound telemetry mode, the parallel modulating switch 30 may be envisioned as open. The signal impressed on the tuned coil is amplified by amplifier 32 and passed through a signal conditioner and decoder 34 which recovers the data signal (FIG. 2) and feeds it serially into shift register 36.

In order to present the transmitted data to the implant's microcomputer, the contents of shift register 36 are read out in parallel through input port 38.

For outbound telemetry, the 64 kHz carrier signal is continuously applied to the transmitter coil 16 in the external programmer to energize the tuned telemetry coil 26. Data for telemetry is presented by the implant at the microcomputer output port 40 and loaded in parallel into shift register 42. The contents of shift register 42 are serially converted to pulsewidth modulation signals by telemetry timing circuit 44. The output of circuit 44 is applied to switch 30 to modulate the impedance of the tuned coil network. The same code format is used so that to telemeter a binary zero, switch 30 is enclosed in effect for two whole cycles of the carrier signal while a binary 1 is signified by loading the transponder for the equivalent of six full carrier cycles.

The signal reradiated or reflected by the implanted transponder coil 26 is picked up by coaxially pickup coils 46 and 48 connected to kilometric telemetry receiver circuit 50. Receiver circuit 50 operates in the same manner described in copending application Ser. No. 153,093 U. S. Pat. No. 4,361,153 to recover the transmitted data by means of a comparative phase detection system. The reliability of this system is increased by virtue of the discrete cycle encoding achieved by synchronizing telemetry with the carrier signal. The phase detected output of receiver 50 is passed via a decoder 52 which forms a standard binary pulse input to shift register 54. The contents of the register 54 are applied in parallel to microcomputer input port 56 to deliver the telemetered data to the external programmer's computer system.

A specific embodiment designed to test the feasibility of the external programmer and implant communications system diagrammed in FIG. 1 is shown in FIGS. 3-6. In the detailed schematic drawings, resistance values are given in ohms, for example, 10K represents 10 kilohms and capacitance is expressed in microfarads unless otherwise indicated. Digital integrated circuits such as CD4040 represent RCA digital CMOS series of standard commercially available circuits. Voltage terminals are +5 volts unless otherwise indicated.

Figure 3:
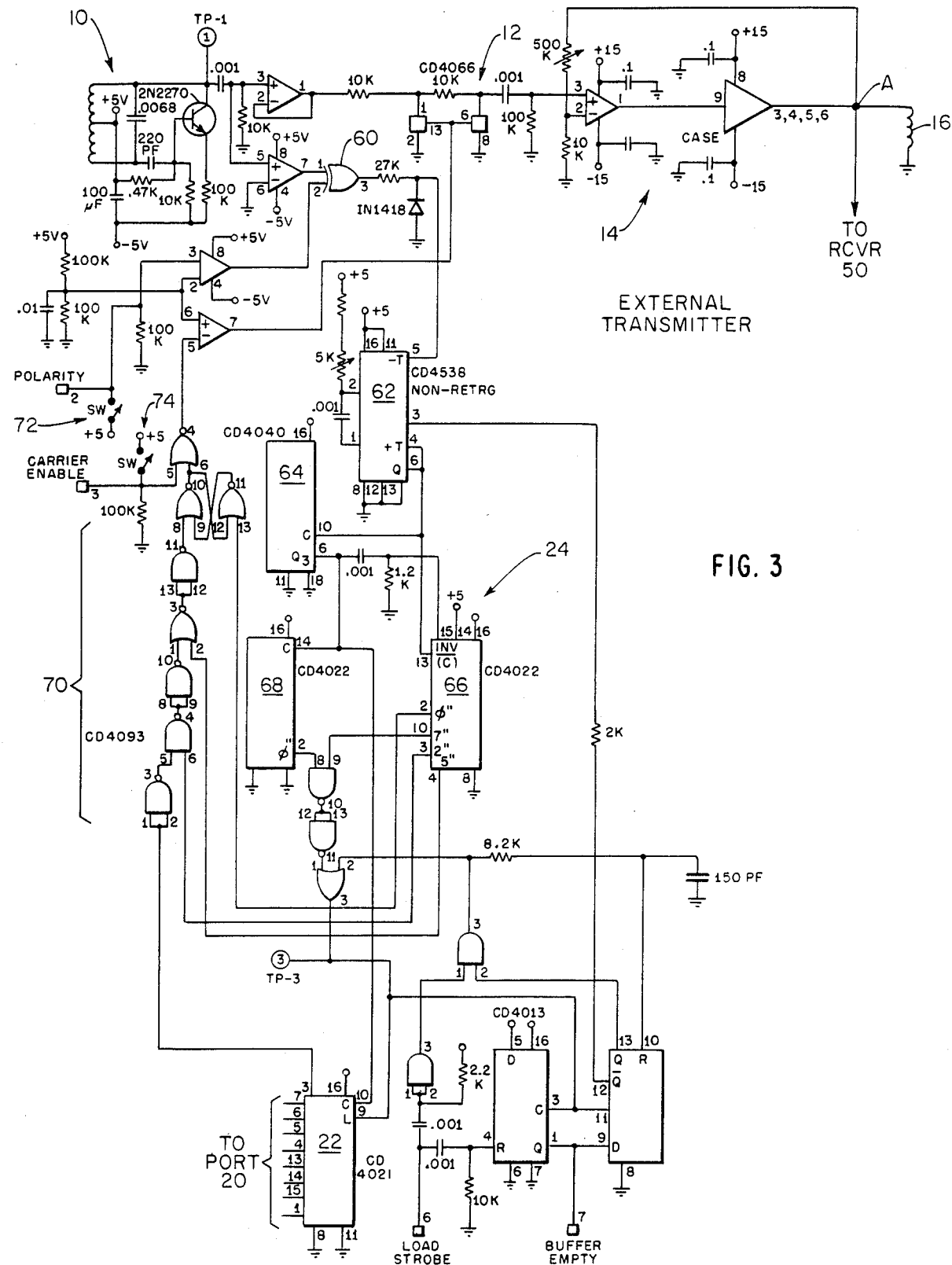
FIG. 3 is a schematic diagram of the external transmitter of FIG. 1.

In FIG. 3, the transistor LC oscillator 10 produces a sinusoidal 64 kHz output coupled by way of an operational amplifier to switch network 12 comprised of a pair of analog switch transmission gates arranged to shunt the signal to ground. Two stage power amplifier 14 supplies the carrier signal to the transmitter coil 16.

The tandem transmission gates comprising switch 12 are gated as follows to provide cycle synchronized pulsewidth modulation of the 64 kHz signal.

A replica of the carrier signal is buffered and passed via an exclusive OR GATE 60 to the inverted trigger input of non-retriggerable one shot 62. The output of one shot 62 clocks binary counter 64 and provides the inverted clock input for first decade counter 66. A second decade counter 68 is clocked by the Q3 output of binary counter 64. The logic is configured so that the "zero" output of decade counter 68 corresponds to the start of the eighth positive cycle of the carrier and the "7" output of the other decade counter 66 indicates that the eighth cycle is finished. Counter 66 counts cycles within the eight cycle bit period of the carrier. Counter 68 keeps track of the number of bit periods and signals when eight bit periods have elapsed to signify the end of a byte at which time the shift register 22 is reloaded.

The Q3 output of binary counter 64 clocks the shift register 22 such that at the beginning of each bit period the next bit in the shift register is presented to logic gates 70. Gates 70 combine a given bit output of the shift register 22 with outputs zero, 2 and 5 of the bit timer 66 such that a zero output from the shift register causes the transmission gates 12 to stop shunting the carrier signal to ground for exactly two whole cycles of the carrier. Similarly, the logic gates 70 cause a "1" output of the shift register 22 to signal the transmission gates 12 to stop shunting the carrier signal for six cycles.

Polarity switch 72 inverts the phase of the synchronizing signal from exclusive OR GATE 60 in connection with a handshake sequence between the programmer and an implant. An example of this type of sequence is described in copending applications Ser. Nos. 195,665, U.S. Pat. No. 4,424,812 and 281,011, U.S. Pat. No. 4,432,360. If the programmer does not receive a correct initial response from the implant, the polarity switch is automatically thrown to reverse the phase of the transmitted code. This will automatically correct for an upside down pacer implantation where the directionality of the transponder coil is exactly reversed, as is sometimes encountered.

Carrier enable switch 74 is automatically actuated when in the telemetry receive mode to remove the shunting effect of switch network 12 so that continuous wave unmodulated carrier signal is supplied to the transmitter coil 16.

The external receiver shown in FIG. 4 taps into the transmitter coil 16 with the voltage divider connected to point A of FIG. 3 to provide a phase reference related to the original carrier signal. The received signal reradiated or reflected by the implanted transponder coil is picked up by coils 46 and 48. The phase detection and decoding circuitry as shown in FIG. 4 operates in the same manner as that described in copending application Ser. No. 153,093, U.S. Pat. No. 4,361,153 and 281,011, U.S. Pat. No. 4,432,360 with the exception that the recovered data from Q1 of dual flipflop 80 is clocked out by a crystal oscillator driven clock circuit 82 as shown in FIG. 4 to provide serial data for entry in shift register 54 of FIG. 1.

Figure 5:
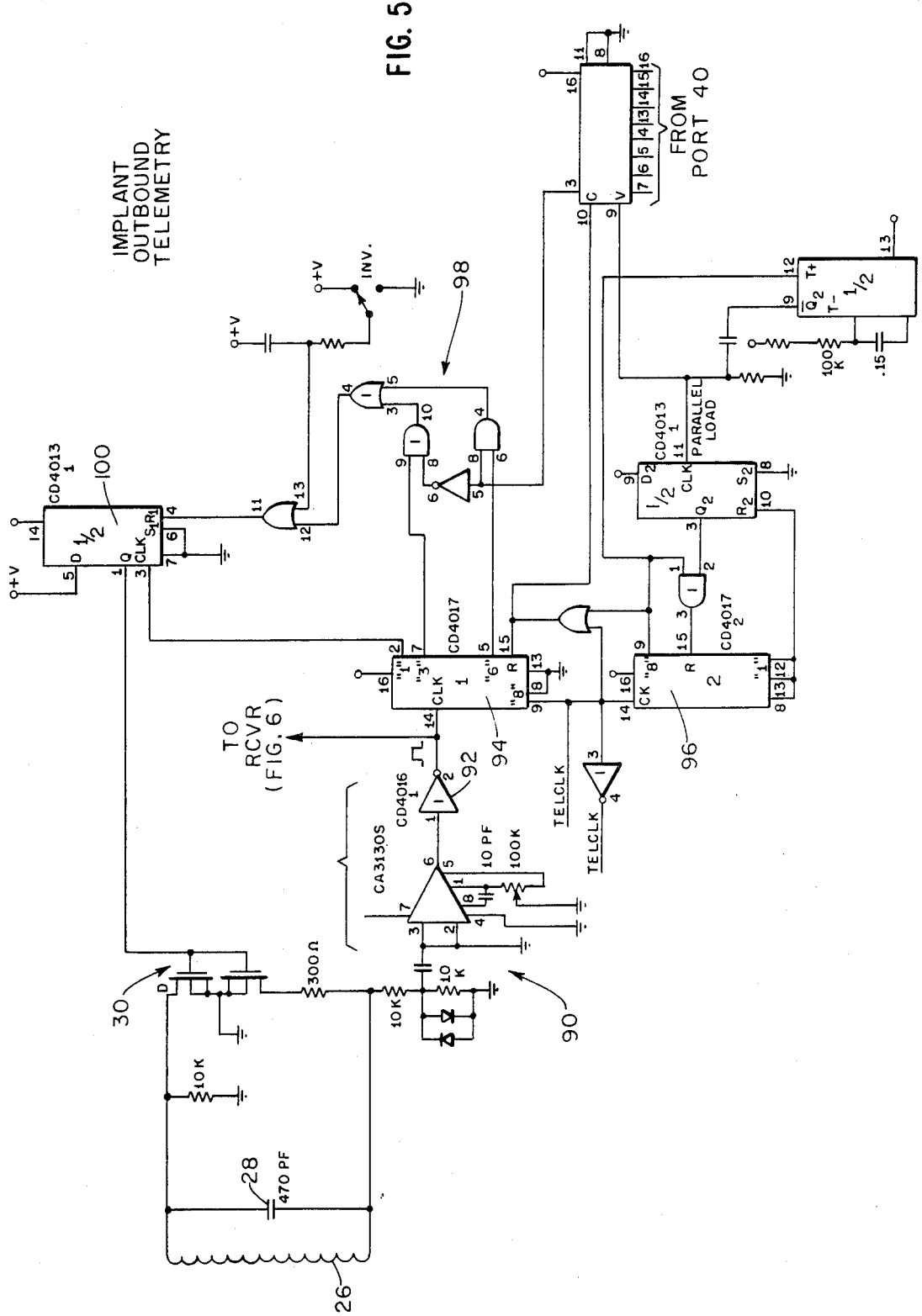
FIG. 5 is a schematic diagram of the implant outbound telemetry system of FIG. 1.

Details of the synchronized outbound telemetry system for the implant are shown in FIG. 5. The carrier signal impressed across the coil 26 is resistively coupled to a comparator 90 which acts a threshold detector. The output of the comparator is inverted to provide a square timing pulse which is used both for synchronizing telemetry as well as to provide the received input for the implant receiver shown in FIG. 6. The output of the inverter 92 corresponds to a positive point in the first quarter cycle of the carrier signal. In the telemetry circuit, the output of inverter 92, marking each cycle of the carrier, forms the clock input to decade counter 94 which serves as the bit timer. The output 7 of the bit timer corresponds to two cycles of the carrier, while the output 5 corresponds to five cycles of the carrier. On the eighth cycle, the bit timer "8" output clocks the shift register 42 and byte timer formed by decade counter 96. When the byte timer counts to eight, it holds the bit timer reset and signals the microprocessor output port to get the next byte from memory. This is accomplished in the test circuit of FIG. 5 by triggering a one-shot output to the load control input of the shift register 42. (A similar technique is used in the external programmer.) The 5 and 7 outputs of the bit timer 94 combine with the serial output of the shift register 42 in gates 98 to form the reset input to flipflop 100. The "1" output of the bit timer 94 is connected to the clock input of the flipflop 100 to synchronize the pulsewidth modulation with the carrier signal. Thus at the beginning of each bit period the transponder gate 30 is actuated to load the transponder coil 26. The gate is released by the reset input to the flipflop 100 after either two or six cycles of the carrier have occurred.

Figure 6:
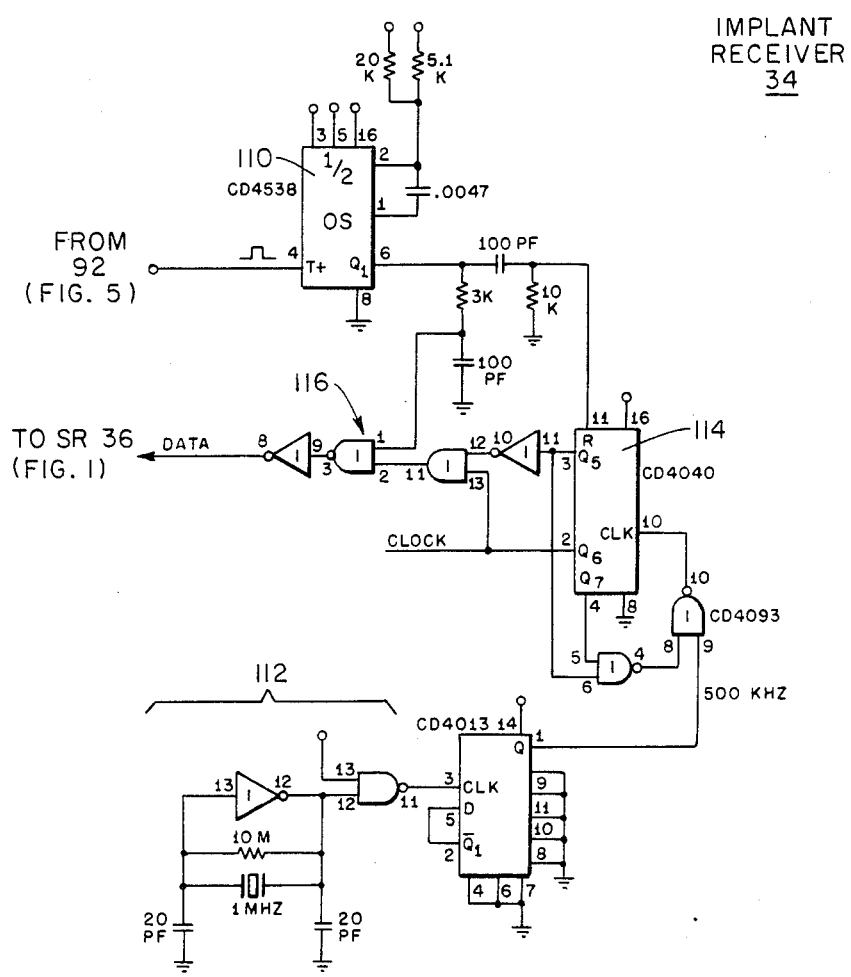
FIG. 6 is a schematic diagram of a portion of the implant data receiver system of FIG. 1.

The implant receiver circuit is shown in detail in FIG. 6. The output of the amplifier/detector circuit 32 of inverter 92 of FIG. 5 is shown in the detector signal line of FIG. 2. This signal is passed to the trigger input of retriggerable one-shot 110 whose output is shown in FIG. 2. The astable period is designed to be somewhat longer than the gap between detector signal pulses so that the Q output of the one-shot 110 will remain high so long as the carrier is present. A crystal oscillator and divide by two circuit 112 clock a binary counter 114 that is reset by the one-shot to produce a sample gate in order to form a "missing pulse detector". The sample gate is timed to occur at an optimum point during the fourth carrier cycle of each bit period so that if a zero has been transmitted there will be no one-shot output at that point; while if a "1" has been transmitted there will still be a one-shot output at that point. The result is the data output shown in FIG. 2 which is passed to shift register 36 as shown in FIG. 1.

The two-way telemetry system described herein has a number of important advantages. First, it eliminates the use of a reed switch for entering programming data in the implant. While it may still be necessary or desirable in some applications to have a reed switch for magnet rate or diagnostic purposes, for example, in a cardiac pacer, the noncyclical operation of the reed switch makes it possible to use a switch of less critical design. Of course, the diagnostic mode could be accessed by carrier modulation with a suitable code. Eliminating the magnetic impulse programming system also has the advantage of reducing the size and weight of the programming as well as conserving current. Making dual use of the transponder coil as well as the transmitter coil in the programmer saves space and lowers the part count compared to alternative data transmission mechanisms. Perhaps even more importantly, using the 64 kHz modulated signal increases the data rate. The synchronous modulation signal overcomes the greater attenuation of the can at the higher frequency. In addition, deriving the clock signals from the transmitted or received carrier itself, avoids timing errors.

The above described circuitry can be varied and modified in many respects without departing from the underlying principles of the invention. For example, synchronous modulation of the carrier can be used for either inbound or outbound telemetry of both. While designed for cardiac pacers having microcomputers, the system is obviously applicable to other types of implants having discrete logic in hardware form. Moreover, other types of synchronized modulation based on the carrier cycles may be useful in different applications. Of course, many of the data timing functions performed by discrete logic in the embodiments shown in FIGS. 3–6 could alternatively be performed by computer software if desired. The carrier frequency 64 kHz was chosen as the minimum necessary to obtain a data rate acceptable for intracardiac ECG transmission. However, in systems having lower data rate requirements, the carrier frequency may be beneficially lowered, particularly where the attenuation from the metallic enclosure is lessened by doing so.

What is claimed is:

1. A two-way telemetry system for a biomedical implantable device including means for providing an externally generated carrier signal, comprising
an implantable enclosure,
a telemetry coil tuned to said carrier signal and mounted within said enclosure,
a low impedance shunt circuit connected across said tuned coil including semiconductor means for modulating the impedance of said shunt circuit in accordance with a digital information signal to alter the phase and amplitude of a signal that is reradiated by said tuned coil in the presence of said externally generated magnetic carrier signal at said carrier frequency,
detector means coupled to said telemetry coil for producing an output related to each successive cycle of said carrier signal, and
telemetry timing means responsive to said detector means output for producing said digital information signal to said shunt circuit in a predetermined synchronized relationship with the cycles of said carrier signal,
said telemetry timing means including means for counting the number of cycles of said carrier signal and for establishing a relationship between the data of said digital information signal and the number of cycles of said carrier signal,
said timing means further including means for actuating said shunt circuit in a first condition for a predetermined number of cycles of said carrier signal and in a second condition for a predetermined different second number of cycles of said carrier signal.

2. The system of claim 1, wherein said timing means further includes means for establishing a bit period composed of a predetermined third number of cycles of carrier signal.

3. The system of claim 2, wherein the first, second and third predetermined numbers of cycles are progressively greater.

4. The system of claim 3, wherein each of the first, second and third numbers of cycles is an integer less than 10.

5. The system of claim 1, wherein said carrier frequency is 64 kHz.

6. The system of claim 4, wherein said carrier signal is 64 kHz.

7. The system of claim 6, wherein said first, second and third predetermined numbers of carrier cycles are 2, 6 and 8 respectively.

8. The system of claim 1, further comprising decoding means responsive to the output of said detector means for recovering a modulation signal externally impressed upon said carrier signal.

9. The system of claim 8, wherein said decoding means has means for decoding pulsewidth modulated bursts of carrier signal.

10. The system of claim 8, wherein said decoding means includes missing pulse detecting means.

11. An external programming data transmitter for a biomedical implant, comprising
oscillator means for generating a continuous wave carrier signal of constant frequency,
transmitting means responsive to application of said carrier signal for transmitting said signal to an implant in the body of a patient,
gate means responsive to a control signal for gating said carrier signal to said transmitter means,
means responsive to said oscillator means output for producing a sync signal indicative of the same relative point in each successive cycle of said carrier signal, and
modulation means responsive to said sync signal for producing a first condition in said control signal for a first predetermined number of cycles of said carrier in response to a first condition of a data signal and for producing a second condition of said control signal for a second predetermined number of cycles of carrier signal in response to a second condition of a data signal.

12. The system of claim 11, wherein said modulation means further includes means for establishing a predetermined bit period of a third predetermined number of cycles of the carrier signal.

13. The system of claim 12, wherein said first, second and third predetermined numbers of cycles are less than 10.

14. The system of claim 11, wherein said carrier frequency is 64 kHz.

15. The system of claim 12, wherein said carrier frequency is 64 kHz.

16. The system of claim 15, wherein said first, second and third predetermined numbers of cycles are 2, 6 and 8, respectively.

17. The system of claim 11, further comprising
means for reversing the phase of said sync signal on command to invert the polarity of the transmitted signal.

18. A two-way telemetry system for a biomedical implant, comprising
an external communications module having oscillator means for producing a continuous wave carrier signal at a constant frequency,
transmitter coil means,
gate means responsive to the output of the said oscillator means for producing a sync signal indicative of approximately the same point in successive cycles of carrier signal, and
modulator means responsive to said sync signal for producing said control signal in one condition to said gate means for a predetermined number of cycles of carrier in response to a data input in one condition and for producing said control signal in a separate condition for a second predetermined number of cycles of carrier signal in response to a data input of a second condition whereby pulsewidth, cycle synchronized modulated bursts of carrier signals are transmitted,
said external communications module further including pickup coil means, and means responsive to the output of said pickup coil means for producing an output indicative of relative phase shift of the output of said pickup coil means, and decoding means for recovering data from the output of said first detector means, and
an implantable enclosure,
a communications module mounted within said enclosure, including a telemetry coil tuned to said carrier frequency, a low impedance shunt circuit connected across said tuned coil including semiconductor means for modulating the impedance of said shunt circuit in accordance with a digital information signal to alter the phase and amplitude of a signal reradiated by said tuned coil in the presence of said carrier signal, second detector means coupled to said telemetry coil for producing a signal indicative of approximately the same point in each cycle of said carrier signal, missing pulse detector means responsive to the output of said second detector means for recovering transmitted data modulating said carrier signal, data timing means for producing said information signal to said shunt circuit, responsive to the output of said second detector means, in one condition for a first predetermined number of cycles of said carrier in accordance with data in one condition and for producing the information signal in a second condition for a second predetermined number of cycles of said carrier signal when the data is in a second condition.

* * * * *